(12) United States Patent
Tuke et al.

(10) Patent No.: US 8,419,800 B2
(45) Date of Patent: Apr. 16, 2013

(54) PROSTHESIS

(75) Inventors: Michael Antony Tuke, Guildford (GB); Andrew Clive Taylor, Nr Chichester (GB)

(73) Assignee: Finsbury (Development) Limited, Leatherhead, Surrey (GB)

(*) Notice: Subject to any disclaimer, the term of this patent is extended or adjusted under 35 U.S.C. 154(b) by 106 days.

(21) Appl. No.: 12/116,708

(22) Filed: May 7, 2008

(65) Prior Publication Data
US 2009/0005878 A1    Jan. 1, 2009

(30) Foreign Application Priority Data

Jun. 26, 2007 (EP) .................................... 07111092
Feb. 28, 2008 (GB) .................................... 0803676.6

(51) Int. Cl.
*A61F 2/32* (2006.01)
(52) U.S. Cl.
USPC ........................................................ 623/22.21
(58) Field of Classification Search .... 623/22.21–22.26, 623/22.32, 22.35, 22.38, 22.15–22.2, 22.39, 623/18.11, 19.12–19.14
See application file for complete search history.

(56) References Cited

U.S. PATENT DOCUMENTS

| | | | | |
|---|---|---|---|---|
| 3,894,297 A * | 7/1975 | Mittelmeier et al. | ...... | 623/22.14 |
| 4,566,138 A * | 1/1986 | Lewis et al. | ............. | 623/22.38 |
| 4,666,449 A | 5/1987 | Frey et al. | | |
| 5,080,678 A | 1/1992 | Spotorno et al. | | |
| 5,098,437 A | 3/1992 | Kashuba et al. | | |
| 5,549,700 A * | 8/1996 | Graham et al. | ............ | 623/22.14 |
| 5,658,338 A * | 8/1997 | Tullos et al. | ............... | 623/22.39 |
| 5,879,397 A * | 3/1999 | Kalberer et al. | ........... | 623/22.25 |
| 5,904,688 A | 5/1999 | Gilbert et al. | | |
| 5,919,236 A * | 7/1999 | Pfaff et al. | ................. | 623/18.11 |
| 5,928,287 A | 7/1999 | Keller | | |
| 5,954,727 A | 9/1999 | Collazo | | |
| 6,132,469 A * | 10/2000 | Schroeder | .................... | 623/22.24 |
| 6,610,097 B2 * | 8/2003 | Serbousek et al. | ......... | 623/22.24 |
| 6,758,864 B2 * | 7/2004 | Storer et al. | ............... | 623/22.38 |
| 6,976,999 B2 * | 12/2005 | Charlebois et al. | ........ | 623/16.11 |
| 7,794,504 B2 * | 9/2010 | Case | ......................... | 623/22.21 |
| 2003/0050705 A1 * | 3/2003 | Cueille et al. | .............. | 623/22.24 |
| 2003/0105529 A1 * | 6/2003 | Synder et al. | .............. | 623/22.24 |
| 2004/0098127 A1 * | 5/2004 | Charlebois et al. | ........ | 623/16.11 |
| 2004/0186586 A1 | 9/2004 | Seyer et al. | | |
| 2005/0102033 A1 | 5/2005 | Lambert et al. | | |
| 2005/0240276 A1 | 10/2005 | Shea et al. | | |
| 2007/0239283 A1 * | 10/2007 | Berger et al. | .............. | 623/22.29 |
| 2009/0082868 A1 * | 3/2009 | Cordaro et al. | ........... | 623/17.16 |
| 2009/0093887 A1 * | 4/2009 | Walter et al. | .............. | 623/22.11 |
| 2009/0248168 A1 * | 10/2009 | Tuke et al. | ................. | 623/22.24 |
| 2009/0287312 A1 * | 11/2009 | Berger et al. | .............. | 623/22.29 |

FOREIGN PATENT DOCUMENTS

| | | |
|---|---|---|
| DE | 10250390 A1 | 5/2004 |
| EP | 1634552 A2 | 3/2006 |
| EP | 1721586 A1 | 11/2006 |
| GB | 2323036 A | 9/1998 |

OTHER PUBLICATIONS

European Search Report in EP08103809, dated Aug. 6, 2009.

* cited by examiner

*Primary Examiner* — Alvin J. Stewart
(74) *Attorney, Agent, or Firm* — Senniger Powers LLP

(57) ABSTRACT

A preassembled acetabular cup prosthesis comprising an outer shell and a ceramic liner located within the shell, said preassembled unit having been assembled ex-vivo under a controlled force selected to optimize the pre-stressing of the components of the prosthesis.

15 Claims, 3 Drawing Sheets

PROSTHESIS

FIELD OF THE INVENTION

The present invention relates to a prosthesis. More particularly, it relates to a preassembled acetabular component for a hip prosthesis and a process for the production thereof.

BACKGROUND OF THE INVENTION

The efficient functioning of the hip joint is extremely important to the well-being and mobility of the human body. Each hip joint is comprised by the upper portion of the femur which terminates in an offset bony neck surmounted by a ball-headed portion which rotates within the acetabulum in the pelvis. Diseases such as rheumatoid- and osteo-arthritis can cause erosion of the cartilage lining of the acetabulum so that the ball of the femur and the hip bone rub together causing pain and further erosion. Bone erosion may cause the bones themselves to attempt to compensate for the erosion which may result in the bone becoming misshapen.

Operations to replace the hip joint with an artificial implant are well-known and widely practiced. Generally, the hip prosthesis will be formed of two components, namely: an acetabular component which lines the acetabulum; and a femoral component which replaces the femoral head. The femoral component may be total femoral head replacement in which case the component includes a head, neck and a stem which in use in inserted into the end of a prepared femur. Alternatively, where appropriate, the femoral head component may be a resurfacing prosthesis which is attached to the head of the femur once it has been suitably machined.

In an operation to insert a prosthetic acetabulum in a patient's pelvis the surgeon first uses a reamer to cut a cavity of appropriate size in the patient's pelvis. An acetabular cup is then inserted into the cavity. By "appropriate size" is meant a size which is selected by the surgeon as being the most appropriate for that particular patient. Normally, it is desirable to retain as much of the original healthy bone surface as possible.

Commercially available acetabular cups are sold in a range of sizes to suit the needs of individual patients. Generally, acetabular cups are available in sizes of from 42 mm to 62 mm diameter with 2 mm increments between neighboring sizes.

There are a number of different types of prosthetic acetabular cups. One type of cup is those made from polyethylene. They are generally cemented into the acetabulum and require only light pressure to seat them in the cement.

One alternative cup type has a polyethylene liner unit for articulation with the femur and a metal shell for insertion into the pelvic cavity. These cups with metal shells may be implanted without cement such that they rely on a jam fit between the metal shell and the patient's acetabulum. However, in some arrangements, screws may be used to secure the cup shell in position in the pelvis before the liner is applied into position. The insertion of the metal shell into the pelvis requires considerable force. As the surgeon applies this force, there is a risk that the metal shell can become damaged or deformed. There is also a possibility that during the application of the force, the shell may be moved so that it is not in the optimum alignment in the acetabulum. Often the metal shells have outer surfaces or coatings which encourage bone to grow into them over time.

With this type of prosthesis, the polyethylene liner unit is snapped or screwed into the metal shell after the metal shell has been seated in the acetabulum. Thus the inner surface of the liner forms the socket part of the joint.

More recently, ceramics have been used to as an alternative to the plastics liner. In this arrangement, the metal shell, which is generally formed from titanium and which is of a similar thickness to the arrangement in which a polyethylene liner is used, is inserted into the acetabulum. The ceramic liner is then inserted into the shell. It can be difficult for the liner to be accurately aligned in the shell. In addition, this insertion of the liner does require the application of a considerable force which is usually applied by the surgeon using a mallet often via an insertion tool. Considerable force is generally required to achieve a successful interface. However, this force can damage the ceramic liner.

In order to get an optimum fit, it is necessary that the forces applied for both the insertion of the metal shell and for the ceramic liner are appropriate but not excessive. One problem however, is that to date there has been no understanding as to what forces are appropriate nor is there a means to ensure that the correct force is applied.

The surgeon is not generally able to apply a controlled amount of force applied. Some surgeons may not apply sufficient force in one hit and it may be necessary for a plurality of hits to be used. These may not all strike at the same angle and may not each apply the same force. Other surgeons may apply a much greater single strike. The force applied by the surgeon on, for example, an insertion tool may vary considerably and can be of the order of about 3 to 5 kN but can also be much higher and may even be of the order of about 35 kN.

Whilst very large forces may only be applied for small moments in time, of the order of seconds or fractions of a second, forces of this magnitude, or a plurality of forces of smaller magnitude may cause the shell to be deformed as it is inserted into the acetabulum. This is a particular risk in those arrangement s where the thickness of the shell is only from about 1 mm to about 3 mm thick. If the shell is deformed, it can become difficult or even impossible to insert the liner.

Additionally or alternatively, the liner may be incorrectly seated in the shell which can lead to various disadvantages. Not only is there a risk that where a portion of the liner stands above the rim of the cup, a point of irritation can be produced but also, there is a risk that material, such as wear debris, may congregate against the raised portion of the liner or against the wall of the cup in the area where the liner sits below the rim. This accumulation of debris may provide a site for post-operative infection. Even if the liner is correctly located and the shell is not deformed during the assembly process, it may become deformed on insertion of the prosthesis into the pelvis such that the shell may become spaced from the liner over at least a portion of the prosthesis.

Even if the surgeon is able to accurately seat the liner in the cup, there is a risk that during assembly debris may be caught between the liner and the cup which may effect the wear properties of the prosthesis. A further problem associated with the presence of debris, which may include fluids such as blood or fat, between the shell and liner is that in use, in vivo the presence of the debris may cause the shell and liner to move apart.

Without wishing to be bound by any particular theory, it will be understood where the shell and ceramic liner are held together by friction, debris, in particular fatty substances or blood, can interfere with the frictional interface between the outer surface of the liner and the inner surface of the shell such that there is a propensity for the liner to move out of the shell.

A further problem which may be encountered is that while inserting the liner in the shell it may become damaged. If this damage is a chip or crack on the outer surface of the liner, i.e. on the surface adjacent to the surface of the shell, its presence may not be noticed by the surgeon during assembly. However, its existence will be a point of weakness which can result in the prosthesis failing in use.

It is therefore desirable to provide an acetabular component which reduces the risk of liner misplacement and which has enhanced life expectancy arising, in part, through improved resistance to damage caused during impaction into the acetabulum. It is also desirable to provide an acetabular cup prosthesis which can be easily handled and inserted during surgery without damage to the acetabular cup prosthesis and which minimizes the risk of debris being trapped between the cup and the liner.

SUMMARY OF THE INVENTION

According to a first aspect of the present invention, there is provided a preassembled unit acetabular cup prosthesis comprising: an outer shell; and a ceramic liner located within the shell, said preassembled unit having been assembled ex-vivo under a controlled force selected to optimise the pre-stressing of the components of the prosthesis.

According to a second aspect of the present invention there is provide a method for assembling an acetabular cup prosthesis comprising the steps of: (i) providing a metal shell; (ii) providing a ceramic liner; and (iii) applying the ceramic liner to the shell ex-vivo under a controlled force selected to optimise the pre-stressing of the prosthesis.

BRIEF DESCRIPTION OF THE DRAWINGS

The present invention will now be described, by way of example, with reference to the accompanying drawings.

DETAILED DESCRIPTION OF THE INVENTION

Figure 1:
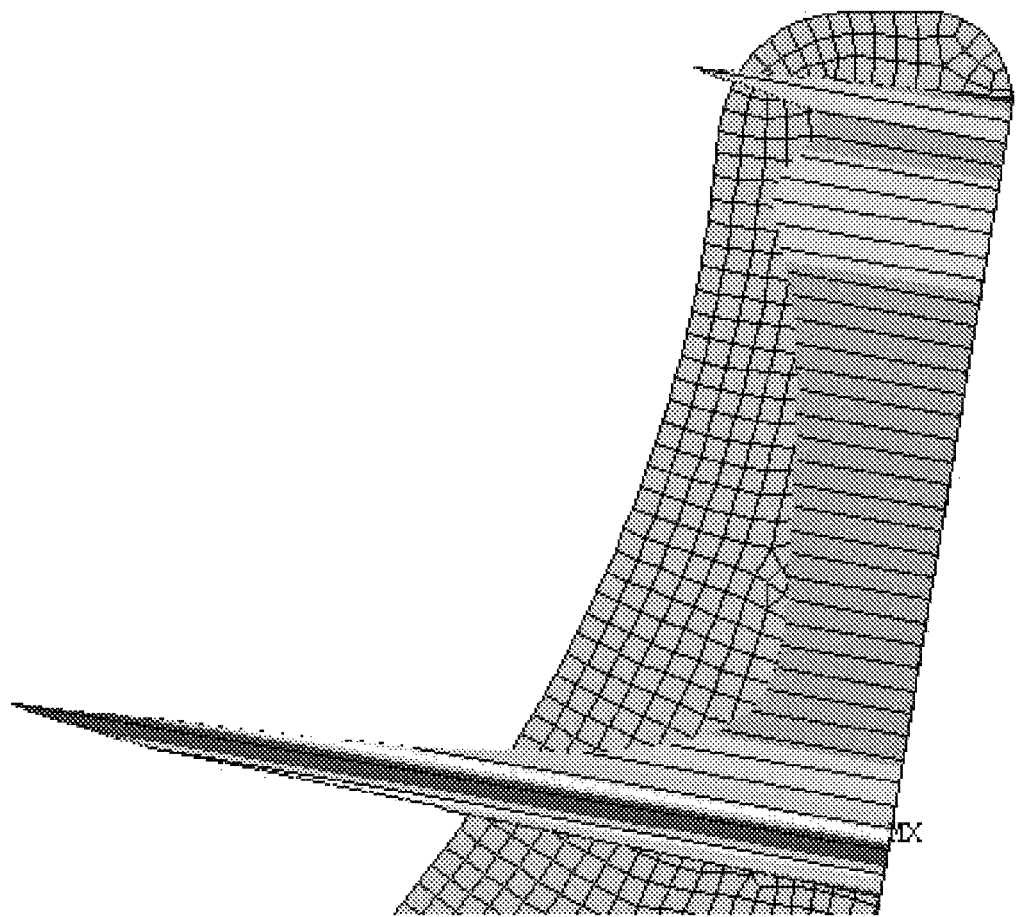
FIG. 1 which shows a typical predicted pressure gradient across the conic interface as a result of the controlled assembly of the present invention.

According to a first aspect of the present invention, there is provided a preassembled unit acetabular cup prosthesis comprising an outer shell; and a ceramic liner located within the shell; said preassembled unit having been assembled ex-vivo under a controlled force selected to optimise the pre-stressing of the components of the prosthesis.

For the purposes of this application, the term "ceramic" should be construed as meaning not only true ceramic materials but also other materials which display ceramic-like properties. Ceramic-like properties for the purposes of the present invention are those where strength, stiffness and rigidity are similar to those of ceramics. Examples of suitable materials include glasses.

Pre-assembling the prosthesis with the controlled force of the present invention provides a prosthesis with improved properties over prior art prosthesis. In particular, the prothesis of the present invention has improved resistance to fracture. In this connection, the ceramic liner of the prosthesis of the present invention will be pre-stressed. This pre-stressing occurs during the controlled assembly process. Unstressed ceramic liners such as those of the prior art, are prone to fracture in use. Stressing of the components of the prosthesis is discussed in more detail below.

Since the unit is preassembled, the liner can be positioned in the outer shell in a controlled manner preferably at the manufacturing site. This will enable the positioning of the liner in the shell to be carefully controlled and checked. Further, the liner can be located within the outer shell in a sterile environment thereby minimising the risk of debris being located between the liner and the outer shell of the prosthesis. Further since assembly is not only ex-vivo, but also generally occurs in an area remote from the patent, there is no risk of blood, fat and the like becoming located between the shell and the liner. This is an important advantage. As discussed above, the presence of such materials in a prosthesis provides a push-off load which can cause separation of the components when loaded in vivo. Thus the prosthesis of the present invention has improved structural integrity in vivo.

The outer shell of the prosthesis is preferably made from metal. Any suitable metal may be used, with titanium being particularly preferred. Cobalt/chromium may also be used. The outer surface of the shell may be configured to promote bone integration. In one arrangement, the outer surface may be coated with a bone growth promoting material such as hydroxyapatite. Any suitable thickness of shell may be used.

In a preferred arrangement, the shell is a titanium shell. In a still preferred arrangement, the titanium shell has a thickness in the region of about 1 mm to about 3 mm.

The ceramic liner may be formed of any material which has acceptable biocompatibility, hardness and wear resistance. Suitable ceramic materials include silicon nitride, doped silicon nitride, an alumina-zirconia ceramic, yttria, stabilized zirconia, ceria, stabilized zirconia, zirconia ceramics, alumina ceramics, oxinium or mixtures thereof. The thickness of the liner is preferably in the region of from about 2 mm to about 5 mm.

In one arrangement, securement means may be formed on the inner surface of the outer shell of the cap, on the liner, or on both such that the liner and the shell are a snap-fit together. In one arrangement some threading may be provided over at least a portion of the mating surfaces so that the liner may be threaded into the shell.

However, in a preferred arrangement, the liner may simply be held in position in the outer cup as a tight fit. In this arrangement it will be the friction between the mating surfaces of the cup and the liner which holds them in position. In this connection, the surface roughness of the inner surface of the shell and that of the outer surface of the liner can be selected to optimise the frictional interplay between the surfaces. In one arrangement the shell may have a surface roughness of its inner surface of from about 1 to about 8 μm, preferably from about 2 to about 5 μm and more preferably from about 2.5 to about 4 μm. The outer surface of the ceramic liner may have a surface roughness of from about 0.5 to about 3 μm, more preferably from about 1 to about 2.5 μm. In one alternative arrangement, coatings may be applied to one or both of the mating surfaces to provide the desired frictional interface. It will be understood that in arrangements relying on friction, other additional connection means may be present.

The inner surface of the outer shell and the outer surface of the liner may be configured so that there is a corresponding taper fit arrangement. Any suitable taper arrangement may be used. In one arrangement, the taper of the shell, which will be a female type taper, will be of the order of from about 15° to about 20° with tapers in the region of 17° to 19° being preferred. The taper of the liner, which will be a male type taper, will be of the order of about 15° to about 20° with tapers in the region of 17° to 19° being preferred. It should be understood that the tapers may not be identical. In one arrangement, the male taper of the liner may be broader than that of the female taper in the shell such that as the liner is applied into the shell it causes some adjustment in the shape of the thin walled shell.

Other processes may be made for joining the prosthesis with the required force and the preferred pre-stressing. In one arrangement, the metal shell may be of a smaller or similar diameter as that of the liner. In this arrangement, the shell may be heated and then the ceramic liner may be forced into position. As the shell cools it will hold the ceramic liner tightly in position.

In one arrangement, a material may be included between the liner and the shell. Suitable materials include acoustic damping materials such as those described in co-pending application GB 0803676.6 which is incorporated herein by reference.

Since the prosthesis of the present invention is preassembled, the orientation/alignment between the shell and the liner can be optimised and controlled such that an improved prosthesis is provided to the patient. In addition, each of the problems identified above is overcome by this arrangement.

A further benefit of the present invention is that at the time of the assembly of the liner in the shell, the force applied can be optimised. The optimisation of the applied assembly force provides an improved prosthesis.

Without wishing to be bound by any theory, it has been found that where a liner is surrounded by a thin shell, there is a risk that the shell can separate from the liner. This can cause a variety of problems including those associated with wear and hence the risk of failure of the prosthesis. In addition, where there is a separation, acoustic ringing of the shell can occur which can be distressing to the patient. In particular, where adverse loading occurs in vivo such that the ball of the femur is articulating against an edge of the prosthetic cup, separation between the shell and the liner at the opposite side of the cup prosthesis may occur.

We have now found that where a force is applied which is selected for the particular materials and thicknesses of the shell and the liner, improved prostheses can be provided. In this arrangement, not only is the shell and liner applied combined correctly, but the loading is optimised.

Where the loading is optimised in this manner, the pre-stressing of the prosthesis is at an optimum and separation will not occur. In this connection it will be understood that the shell being metal is strong in hoop tension whereas the ceramic liner is strong in hoop compression. With the pre-stressing of the present invention, the tensions are optimised. In addition, the compressive interface between the two components is maintained throughout the entirety of the loading envelope in vivo.

A further advantage of the present invention is that the preassembled acetabular cup prosthesis of the present invention has sufficient strength in its preassembled form to withstand the forces supplied during the insertion of the prosthesis into the acetabulum without damage, distortion or separation of the components. In particular, and surprisingly, the sphericity of the prosthesis is substantially maintained even though the diameter is reduced due to the localised compression at the rim of the liner.

The pre-assembled prosthesis of the present invention may be provided with an up action cap. The impaction cap may be pre-assembled with the prosthesis as described in co-pending application EP07111092.8 which is incorporated herein by reference. In one arrangement the impaction cup is configured such that the force applied to impact the prosthesis into the acetabulum is directed via the ceramic liner so that any shock passing through the metal shell is minimised.

According to a second aspect of the present invention, there is provided a method for assembling an acetabular cup prosthesis comprising the steps of (i) providing a metal shell; (ii) providing a ceramic liner; and (iii) applying the ceramic liner to the shell ex-vivo under a controlled force selected to optimise the pre-stressing of the prosthesis.

The force required to optimise the pre-stressing will depend on the materials used for the shell and liner and their respective thicknesses.

For a titanium shell having a thickness of from about 1 mm to about 3 mm in combination with a ceramic liner having a thickness of from about 2 mm to about 5 mm, a force of from about 2 kN to about 7 kN is desirable. The force is preferably about 5 kN. The force is preferably applied by a plate such that it is applied equally across the surface of the prosthesis.

The force applied may be selected in magnitude and direction to cause a desired and pre-selected deformation of the shell to give an optimum combined shell-liner combination.

The acetabular cup prosthesis made according to the method of the second aspect of the present invention is preferably the prosthesis of the above first aspect of the present invention.

To obtain the optimised continuous pressure across the taper joint throughout loading regime to prevent localized separation and increased risk of squeaking and/or accelerated wear various parameters are selected.

The liner material will preferably have a higher Young's modulus than the outer shell. In a ceramic liner, titanium shell combination the Young's modulus will typically be about 350 GPa and 115 GPa respectively. Thus in one arrangement, the ratio between of the Young's Modulus of the liner to the shell will preferably be in the region of from 3:1.

The preload assembly pressure will be selected to achieve the correct initial contact pressure distribution. This is preferably in the region of from 2 to 10 kN.

The outer metal shell will generally be selected to be relative thin to produce a minimum hoop stress and will generally less be about 3 mm or less, preferably from about 2 mm to about 3 mm.

Figure 2:
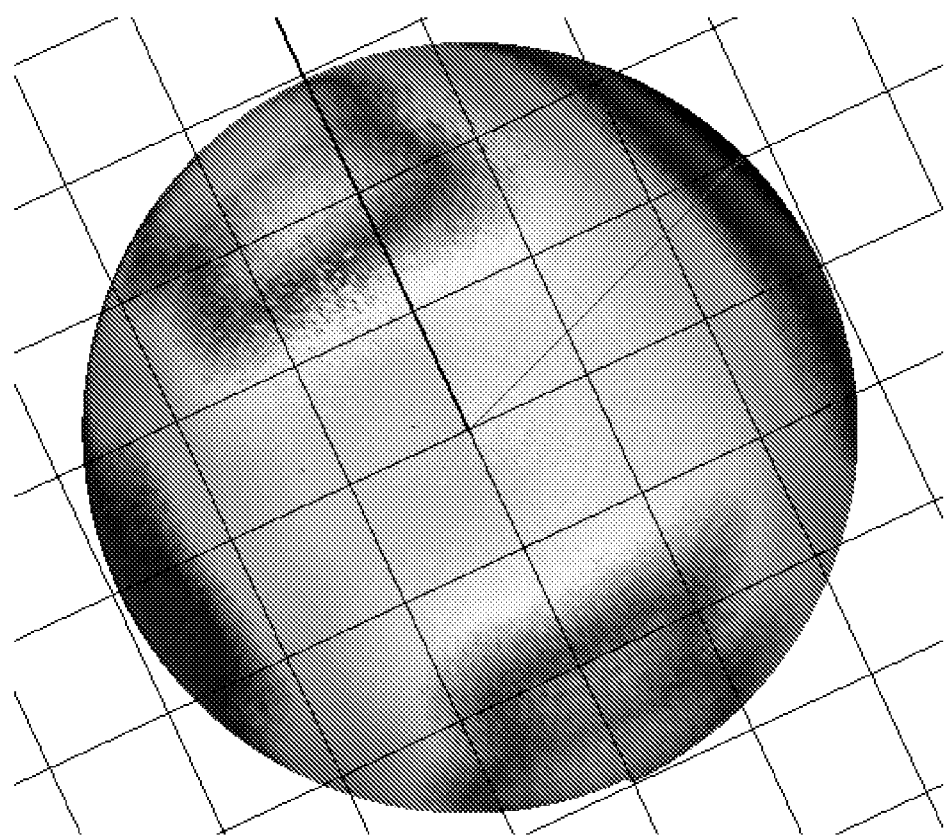
FIG. 2 is an illustration of the sphericity of the prosthesis before assembly.
Figure 3:
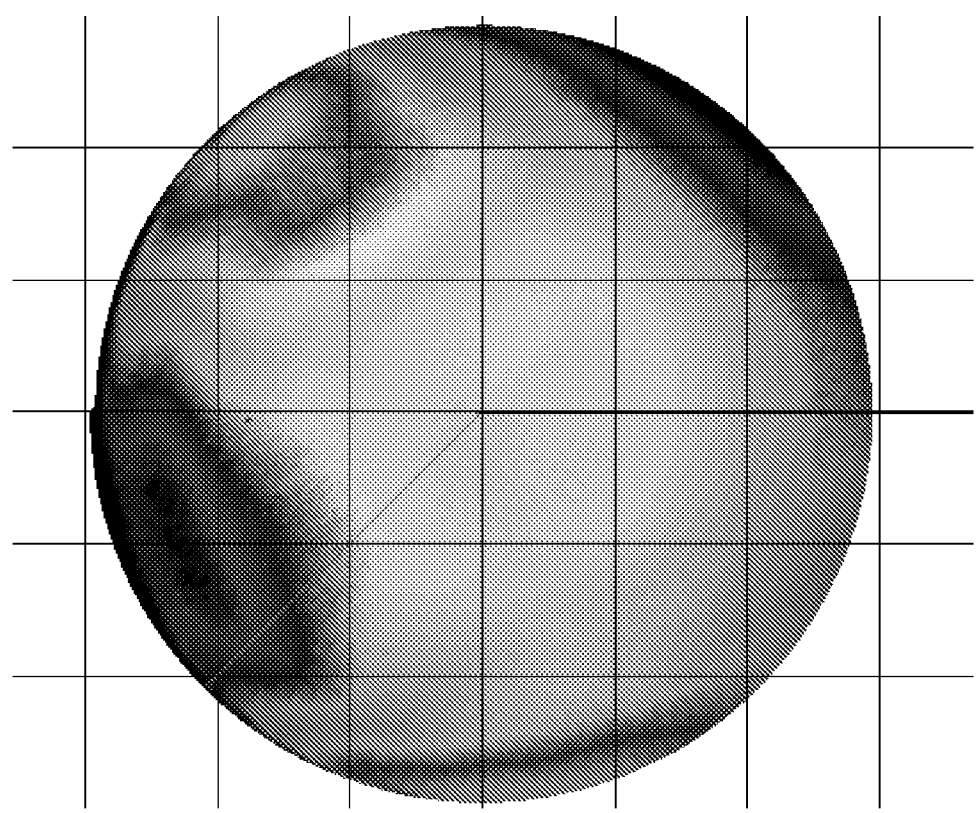
FIG. 3 is an illustration of the sphericity of the prosthesis liner after assembly.

As discussed above during assembly, the sphericity if the prosthesis and hence its components during assembly and/or insertion is maintained even through the diameter is reduced. This is illustrated in FIGS. 2 and 3. In this illustration the cup liner had the nominal size of 48 mm bearing. In FIG. 2, which is pre-assembly, the average radius is 24.0590 mm and the maximum deviation from a true sphere is +2.3/−3.7 µm. As illustrated in FIG. 3, after assembly, the average radius has reduced to 24.0536 mm but the maximum deviation from a true sphere is substantially unchanged at +3.0/−2.8 µm.

What is claimed is:

1. A method for assembling an acetabular cup prosthesis comprising the steps of:
   (i) providing a metal shell having a thickness of about 3 mm or less;
   (ii) providing a ceramic liner having a thickness of about 5 mm or less; and
   (iii) orienting the shell and liner with respect to one another ex vivo such that upon an application of a force the shell and liner come together in a controlled, predetermined orientation;
   (iv) applying the ceramic liner to the shell ex-vivo under a controlled force from about 2kN to about 7kN to pre-stress the shell and liner of the prosthesis.

2. A method according to claim 1 where the metal shell is a titanium shell having a thickness of from about 1 mm to about 3 mm, and the ceramic liner has a thickness of from about 2 mm to about 5 mm.

3. A method according to claim 1 wherein the force is about 5 kN.

4. A method according to claim 1 wherein step (iv) is carried out remotely from a facility in which the acetabular cup prosthesis is to be implanted in a patient.

5. A method according to claim 4 wherein steps i) - iv) are carried out repeatedly prior to any of the assembled shells and ceramic liners being implanted in a patient.

6. A method according to claim 1 wherein step (iv) is carried out in a facility where the acetabular cup assembly is manufactured.

7. A method according to claim 1 wherein the controlled force is applied using a plate such that force is distributed equally across the surface of the prosthesis.

8. A method according to claim 1 further comprising the step of implanting the previously assembled shell and ceramic liner together in a patient.

9. A method according to claim 1 wherein when the ceramic liner is applied to the metal shell the shell is placed in hoop tension and the liner is placed in hoop compression.

10. A method according to claim 1 wherein orienting the shell and liner with respect to one another ex vivo comprises aligning a taper lock arrangement associated with the ceramic liner with a taper lock arrangement associated with the shell.

11. A method for assembling an acetabular cup prosthesis comprising the steps of:

(i) providing a metal shell having a Young's modulus;
(ii) providing a ceramic liner having a Young's modulus greater than the Young's modulus of the shell; and
(iii) orienting the shell and liner with respect to one another ex vivo such that upon an application of a force the shell and liner come together in a controlled, predetermined orientation;
(iv) applying the ceramic liner to the shell ex-vivo under a controlled force from about 2 kN to about 7 kN to pre-stress the shell and liner of the prosthesis.

12. A method according to claim 11 wherein the ratio of the Young's modulus of the ceramic liner to the Young's modulus of the shell is about 3:1.

13. A method according to claim 11 wherein an inner surface of the shell has a surface roughness of from about 1 to about 8 μm.

14. A method according to claim 13 wherein an outer surface of the ceramic liner has a surface roughness of from about 0.5 to about 3 μm.

15. A method according to claim 11 wherein when the ceramic liner is applied to the metal shell the shell is placed in hoop tension and the liner is placed in hoop compression.

* * * * *